United States Patent
Kovacevic et al.

[11] Patent Number: 5,466,686
[45] Date of Patent: Nov. 14, 1995

[54] AMIDES OF 4-OXO-AZETIDINE-2-SULFONIC ACIDS AND SALTS THEREOF, PROCESSES FOR THEIR PREPARATION AND THEIR USE

[75] Inventors: Mice Kovacevic, Slavenskog; Jure J. Herak, Slovenska; Zora Mandic, Vramceva; Irena Lukic, Veslacka; Mirjana Tomic, Zagreb; Zinka Brkic, Gajnice, all of Croatia

[73] Assignee: PLIVA and PLIVA Handels GmbH, Germany

[21] Appl. No.: 115,538

[22] Filed: Sep. 3, 1993

[30] Foreign Application Priority Data

Sep. 8, 1992 [DE] Germany ............... 42 30 053.3

[51] Int. Cl.⁶ .................. A61K 31/395; C07D 205/095; C07D 417/12; C07D 413/12
[52] U.S. Cl. ............................. 514/210; 540/359
[58] Field of Search ................. 540/359; 514/210

[56] References Cited

U.S. PATENT DOCUMENTS 4,771,045   9/1988  Matsuo .................................. 540/355

OTHER PUBLICATIONS

Brkic et al, "Ecologically Rational Development of Chemical Synthesis", Symposium 8–10 Feb. 1993, Zagreb, Abstracts, Poster Session.

*Primary Examiner*—Mark L. Berch
*Attorney, Agent, or Firm*—Pollock, Vande Sande & Priddy

[57] ABSTRACT

The invention relates to the novel 4-oxo-azetidine-2-sulfonic acid amides and their salts of the formula I

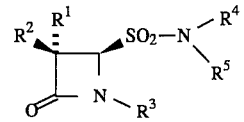

wherein the radicals have the meanings:

$R^1$=hydrogen, halogen;
$R^2$=hydrogen, halogen, $NH_2$, $C_6H_5CH_2CONH$, $C_6H_5OCH_2CONH$, phthalimido, o-MeNHCOC$_6$H$_4$CONH, isoxazolylcarbonylamino;
$R^3$=hydrogen, $Me_2C$=C—COOMe, $H_2C$=C(Me)—CH—COOMe, $Me_2C$=C—$COOCH_2C_6H_5$, $H_2C$=C(Me)CH—$COOCH_2C_6H_4NO_2$-p, $Me_2C$=C—$COOCH_2C_6H_4NO_2$-p, $Me_2C$=C—$COOCH_2C_6H_4$Me-m, $H_2C$=C(Me)—CH—$COOCH_2C_6H_4$Me-m, $Me_2C$=C—COOH;
$R^4$=hydrogen or sodium and
$R^5$=hydrogen, alkyl, benzyl or heterocycle, i.e. isoxazole or pyrazole etc.

The invention also relates to the procedure for the preparation thereof and the use thereof as intermediates in the synthesis of beta-lactam analogs or as active components for the preparations of the drugs for antimicrobial therapy.

29 Claims, No Drawings

AMIDES OF 4-OXO-AZETIDINE-2-SULFONIC ACIDS AND SALTS THEREOF, PROCESSES FOR THEIR PREPARATION AND THEIR USE

The present invention relates to the novel 4-oxo-azetidine-2-sulfonic acid amides and their salts, to processes for the preparation thereof, and the use thereof.

There are described some 4-oxo-azetidine-sulfonic acids, among them the well known are 4-oxo-azetidine-1-sulfonic acids and derivatives thereof [Chemistry in Britain (1983) 302], comprising the important beta-lactam antibiotic Aztreonam [Drugs of the Future 8 (1983) 295].

There are known some 4-oxo-azetidine-2-sulfonic acids, obtained by the transformation of the bicyclic molecules [Angew. Chem. 95 (1983) 912] or by the oxidation of corresponding 4-oxo-azetidine-2-sulfinic acids derivatives [YU pat.application P-240/91], [YU.pat.application P-1390/91] and [EU pat.application 92102335.4/92].

There are also known some 4-oxo-azetidine-2-sulfonic acids derivatives such as acid chlorides [DOS 2,556,071/76], esters [Croat. Chem. Acta 62 (1989) 521–527] and thioesters [J. Chem. Soc. Chem. Commun. 23 (1972) 1304–1305].

According to the data on Prior Art, known to the applicant, there have not been known 4-oxo-azetidine-2-sulfonic acid amides and the salts thereof.

The object of the present invention are novel 4-oxo-azetidine-2-sulfonic acid amides and their salts of the general formula I,

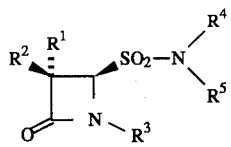

wherein the radicals have the meanings:

$R^1$=hydrogen, halogen;

$R^2$=hydrogen, halogen, $NH_2$, $C_6H_5CH_2CONH$, $C_6H_5OCH_2CONH$, phthalimido, o-MeNHCOC$_6$H$_4$CONH, isoksazolylcarbonylamino;

$R^3$=hydrogen, $Me_2C=C-COOMe$, $H_2C=C(Me)-CH-COOMe$, $Me_2C=C-COO-CH_2C_6H_5$, $H_2C=C(Me)-CH-COOCH_2C_6H_4-NO_2$-p, $Me_2C=C-COO-CH_2-C_6H_4NO_2$-p, $Me_2C=C-COOCH_2C_6H_4Me$-m, $H_2C=C(Me)-CHCO-OCH_2-C_6H_4$-Me-m, $Me_2C=C-COOH$;

$R^4$=hydrogen or sodium and $R^5$=hydrogen, alkyl, benzyl or heterocycle e.g. isoxazole, pyrazole etc.

A further object of the present invention is a process for the preparation of novel 4-oxo-azetidine-2-sulfonic acid amides of the general formula I, wherein the radicals have the afore-said meanings, and which is performed by oxidation of 4-oxo-azetidine-2-sulfinic acid amides and the salts thereof of the general formula II,

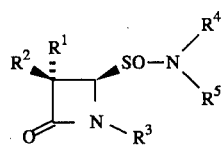

wherein the radicals have the meanings;

$R^1$=hydrogen or halogen;

$R^2$=hydrogen, halogen, $NH_2$, $C_6H_5CH_2CONH$, $C_6H_5OCH_2CONH$, phthalimido, o-MeNHCOC$_6$H$_4$CONH, isoksazolylcarbonylamino;

$R^3$=hydrogen, $Me_2C=C-COOMe$, $H_2C=C(Me)-CH-COOMe$, $Me_2C=C-COOCH_2C_6H_5$, $H_2C=C(Me)-CH-COOCH_2C_6H_4-NO_2$-P, $Me_2C=C-COOCH_2C_6H_4NO_2$-p, $Me_2C=C-COOCH_2C_6H_4Me$-m, $H_2C=C-(Me)-CHCOOCH_2C_6H_4Me$-m, $Me_2C=C-COOH$;

$R^4$=hydrogen and $R^5$=hydrogen, alkyl, benzyl or heterocycle e.g. isoxazole, pyrazole etc.

Oxidation is being carried out with the known oxidizing agents in organic chemistry such as hydrogen peroxide, peracetic acid, m-chloroperbenzoic acid and potassium permanganate, in an acidic or neutral, aqueous or aqueous-organic medium at a temperature of 0° to 100° C. The reaction conditions, molar ratio and isolation of the product in all examples are conventional. Depending on the reactants used in the oxidation as well as molar ratio and temperature range, the various 4-oxo-azetidine-2-sulfonic acid amide derivatives are obtained as illustrated in the following examples. Depending on the way of isolation, 4-oxo-azetidine-2-sulfonic acid amides are obtainable as free amides or their inorganic salts. Amino and carboxyl protective group are cleaved by means of conventional methods.

Sulfinamides of the general formula II. are obtained by the reaction of the corresponding sulfinylchloride and amine as stands in SAD.pat. 4,052,387 (1977). Sulfinylchloride may be obtained in situ starting from penicilline sulfoxide as stands in U.S. Pat. No. 4,081,440(1978) or from sulfinic acid as described in Croat. Chem. Acta 62 (1989) 521.

Another object of the present invention is the use of the said compounds as useful intermediates in the preparation of various beta-lactamic analogues, especially novel bicyclic species.

A further object of the present invention is the use of the said compounds as a potential active material in ready-for-use pharmaceuticals having antimicrobial activity.

The present invention is illustrated by the following examples.

Example 1

(2R,3R) 1-(1'-Methyloxycarbonyl-2'-methyl-prop-1'-enyl)-2-benzylaminosulfonyl-3-phenoxyacetamido-4-oxo-azetidine To a solution of methyl ester of (5R,6R) 6-phenoxy-acetamidopenicillanate sulfoxide (1.9 g, 5 mmole) in dried toluene (215 mL) were added calcium oxide (1.65 g, 28.4 mmole) and N-chlorosuccinimide (0.85 g, 6.4 mmole) and stirred under the stream of nitrogen at boiling within 1.5 hours. The reaction mixture was cooled to 0° C., benzylamine (2.26 g, 21 mmole) was added and stirred for further 2 hours. Reaction mixture was filtered, mother liquor washed with water (2×90 mL), dried ($Na_2SO_4$), filtered and evaporated in vacuum. The residue was chromatographed over a silicagel by eluting with methylene chloride-methanol (20:1). The obtained epimeric mixture (1.8 g, 74.4%) of (2R,3R) 1-(1'-methyloxycarbonyl-2'-methyl-prop-1'-enyl)-2-benzylaminosulfinyl-3-phenoxy-acetamido-4-oxo-azetidine [isomer in excess $^1$H NMR ($CDCl_3$)δ:2.13 and 2.26(6H 2s, $CMe_2$), 3.75(3H, s, OMe), 4.13– 4.50(5H, m, $CH_2N$, $CH_2O$, SNH), 4.95(1H, d, J 5.0 Hz, $C_2H$), 5.87(1H, dd, J 5.0 and 10.0 Hz, $C_3H$), 6.75–7.37(5H, m, $C_6H_5O$), 8.47(1H, d, J 10.0 Hz, CONH) ppm] was dissolved in methylene chloride (35 mL) and formic acid (7 mL), there was added 3o % aqueous solution of $H_2O_2$ (28 mL) and reaction mixture stirred at room temperature within 6 hours. The organic layer was separated, washed with water, dried ($Na_2SO_4$), filtered and evaporated giving foamy residue (1.98 g, 95%): $R_f$ 0.55 ($CH_2Cl_2$: MeOH=20:1); IR (KBr) 3420–3230m, 1785s, 1735m, 1690s, 1605m, 1530m, 1495m, 1440m, 1370m, 1335m, 1225s, 1162s, 1065s, 995w $cm^{-1}$; $^1H$ NMR ($CDCl_3$) δ: 2.09 and 2.25(6H, 2s, $CMe_2$), 3.69(3H, s, OMe), 4.09–4.41(5H, m, $CH_2N$, $CH_2O$, SNH), 4.80(1H, d, J 5.3 Hz, $C_2H$), 5.83(1H, dd, 5.3 and 10.8 Hz, $C_3H$), 6.87–7.44(5H, m, $C_6H_5O$), 7.77(1H, d, J 10.8 Hz, CONH) ppm.

Example 2

(2R,3R) 1-(1'-Methyloxycarbonyl-2'-methyl-prop-2'-enyl)-2-[(5' -methyl-isoxazol-3'-yl)aminosulfonyl]-3-phenoxyacetamido-4-oxo-azetidine Methyl ester of (5R,6R) 6-phenoxyacetamidopenicillanate sulfoxide (1.9 g, 5 mmole) was treated with N-chlorosuccinimide according to the procedure in example 1., thereafter 3-amino-5-methyl-isoxazole (2.06 g, 21 mmole) was added instead of benzylamine. The epimeric mixture of (2R,3R) 1-(1'-methyl-oxycarbonyl- 2'-methyl-prop-2'-enyl)-2-[(5'-methyl-izoksazol-3'-yl)-aminosulfinyl] -3-phenoxyacetamido-4-oxo-azetidine was isolated after stirring and treating of the reaction mixture. Upon evaporation of toluene the epimer with m.p. 185°–190° C. crystallised [$^1H$ NMR ($CDCl_3$) δ: 1.99(3H, s, Me), 2.15(3H, s, Me-isoxazole), 3.85(3H, s, OMe), 4.43(2H, bs, $OCH_2$), 5.05(1H, s, NCHCO), 5.09 and 5.27(2H, 2bs, $=CH_2$), 5.37(1H, d, J 4.5 Hz, $C_2H$), 5.79(1H, s, CH-isoxazole 5.84(1H, dd, J 4.5 and 9.5 Hz, $C_3H$), 6.95–7.34(5H, m, $C_6H_5O$), 7.70(1H, d, J 9.5 Hz, CONH), 8.29(1H, s, SNH) ppm; Anal. $C_{21}H_{23}O_8N_4S$ calc.: C, 52.42; H, 5.82; N, 12.02; S, 6.34%; found: C, 52.93; H, 5.08; N, 11.76; S, 6.73%]. The aspirated crystal was dissolved in methylene chloride and formic acid and then oxidized with hydrogen peroxyde analogously to the procedure in example 1. giving a foamy product: $R_f$ 0.20 ($CH_2Cl_2$:MeOH=20:1 ); IR (KBr)3400-3000m, 1795vs, 1750s, 1690m, 1620m, 1605m, 1535-1494s, 1465m, 1440m, 1245s, 1165s, $cm^{-1}$; $^1H$ NMR ($CDCl_3$) δ:1.91(3H, s, Me), 2.18(3H, s, Me-isoxazole), 3.79(3H, s, OMe), 4.44(2H, bs, $OCH_2$), 4.90(1 H, s, NCHCO), 5.00 and 5.17(2H, 2bs, $=CH_2$), 5.46(1H, d, J 5.0 Hz, $C_2H$), 6.01(1H, dd, J 5.0 and 10.3 Hz, $C_3H$), 6.82–7.41(5H, m, $C_6H_5O$), 7.75(1H, d, J 10.3 Hz, CONH) ppm.

Example 3

(2R, 3R) 1-(1'- Methyloxycarbonyl-2'-methyl-prop-1'-enyl)-2-[(5' -methyl-isoxazol-3'-yl)aminosulfonyl]-3-phenoxyacetamido-4-oxo-azetidine The sulfinamide (m.p.185°–190° C.), prepared according to the procedure in example 2. was dissolved in methylene chloride and stirred with triethylamine for 2 hours at room temperature. After chromatography of the crude product on a silica gel column (2R,3R) 1-(1'-methyloxycarbonyl-2'-methyl-prop-1'-enyl)-2-[ (5'-methyl-isoxazol-3'-yl)-aminosulfinyl]-3-phenoxyacetamido-4-oxo-azetidine was obtained in 80 % yield [$^1$ H NMR ($CDCl_3$) δ:2.06 and 2.19(6H 2s, $CMe_2$), 2.25(3H, s Me-isoxazole), 3.76(3H, s, OMe), 4.31 and 4.40(2H, ABq, J 15.0 Hz, $OCH_2$), 5.34(1H, d, J 5.0 Hz, $C_2H$), 5.80(1H, s, CH-isoxazole), 5.60(1H, dd, J 5.0 and 8.8 Hz, $C_3H$), 6.84–7.32(5H, m, $C_6H_5O$), 7.92(1H, d, J 8.8 Hz, CONH), 8.43(1H, s, SNH) ppm],which was then oxidized with hydrogen peroxyde as mentioned in example 1. There was obtained a foamy product in 85 % yield: $R_f$ 0.24 ($CH_2Cl_2$.MeOH=20:1 ); IR (KBr) 1790s, 1735m, 1700s, 1620m, 1540-1495s, 1465m, 1440m, 1380m, 1230s, 1165s $cm^{-1}$; $^1H$ NMR ($CDCl_3$) δ:2.09 and 2.22(6H 2s, $CMe_2$), 2.26(3H, s, Me-isoxazole), 3.71(3H, s, OMe), 4.46 and 4.57(2H, ABJ J 15.0 Hz, $OCH_2$), 4.57(1H, s, SNH) 5.54(1H, d, J 5.2 Hz, $C_2H$), 6.07(1H, s, CH-isoxazole), 6.06(1H, dd, J 5.2 and 10.4 Hz, $C_3H$), 6.95–7.37(5H, m, $C_6H_5O$), 7.76(1H, d, J 10.4 Hz, CONH), ppm.

Example 4

(2R,3R) 1-(1'-p-Nitrobenzyloxycarbonyl-2'-methyl-prop-2'-enyl)-2-[(5' methyl-isoxazol-3'-yl)aminosulfonyl]-3-phthalimido-4-oxo-azetidine p-Nitrobenzyl ester of (5R,6R) 6-phthalimidopenicillanate sulfoxide (1.5 g, 3 mmole) was treated with N-chlorosuccinimide (0.4 g, 3 mmole) as was described in example 1 and 3-amino-5-methyl-isoxazole ( 1.18 g, 12 mmole) was added and reaction mixture stirred for 4 hours at 10° C. The toluene solution was decanted, washed with water, dried, filtered and evaporated in vacuum. The residue was chromatographed on a silica gel column by means of methylene chloride-ethyl acetate (4:1). There was obtained 0.88 g (2R,3R) 1-(1'-p-nitrobenzyl-oxycarbonyl-2'-methyl-prop-2'-enyl)-2-[(5'-methyl-isoxazol- 3'-yl)aminosulfinyl]-3-phthalimido-4-oxo-azetidine [$^1H$ NMR ($CDCl_3$) d: 1.90(3H, s, Me), 2.27(3H, s, Me-isoxazole), 4.76(1H, bs, NCHCO), 4.92 and 5.06(2H, 2bs, $=CH_2$), 5.25(2H, bs, $OCH_2$), 5.67(1H, d, J 5.4 Hz, $C_2H$), 6.09(1H, d, J 5.4 Hz, $C_3H$), 7.20(1H, bs, CH-isoxazole), 7.52 and 8.20(4H, 2d, J 9.04 Hz, $C_6H_4NO_2$), 7.71–7.95(4H, m, phthalimido), and 8.05(1H, bs, SNH) ppm]. The raaction with hydrogen peroxide (12 mL, 30 %-tna aqueous solution) in methylene chloride (15 mL) and formic acid (2 mL) as mentioned in example 1. gave 0.63 g sulfonamide: $R_f$ 0.58 ($CH_2Cl_2$:MeOH=9:1); IR(KBr) 1805s, 1790s, 1735vs, 1615m, 1525m, 1475m, 1390s, 1350s, 1270w, 1170w, 1110w, 720m $cm^{-1}$; $^1H$ NMR ($CDCl_3$) δ:2.02(3H, s, Me), 2.22(3H, s, Me-isoxazole), 4.98(1H, s, NCHCO), 5.09–5.35(4H, m, $=CH_2$, $OCH_2$), 5.57(1H, d, J 4.5 Hz, $C_2H$), 5.76(1H, d, J 4.5 Hz, $C_3H$), 5.97(1H, s, CH-isoxazole), 7.51 and 8.15(4H, 2d, J 8.4 Hz, $C_6H_4NO_2$), 7.69–8.05(4H, m, phthalimido) ppm].

Example 5

(2R,3R) 2-Benzylaminosulfonyl-3-phenylacetamido-4-oxo-azetidine p-Nitrobenzyl ester of (5R,6R) 6-phenylacetamidopenicillanate sulfoxide (2.10 g, 4.3 mmole) was treated with N-chlorosuccinimide (0.72 g, 5.4 mmole) as was described in example 1. and thereafter with benzylamine (1.5 mL) giving epimeric mixture of (2R,3R) 1-(1'-p-nitrobenzyloxycarbonyl-2'-methyl-prop-1' -enyl)-2-benzylaminosulfinyl-3-phenylacetamido-4-oxo-azetidine ( 1.78 g, 69.4 %) [the epimer in excess $^1H$ NMR (DMSO-$d_6$) δ:2.11 and 2.25(6H 2s, $CMe_2$), 3.53(2H, s, $CH_2CO$), 3.81–4.36(3H, m, $SNHCH_2$), 4.78(1H, d, J 5.4 Hz, $C_2H$), 5.24(2H, bs, $OCH_2$), 5.70(1H, dd, J 5.4 and 9.0 Hz, $C_3H$), 6.65(1H, d, J 9.0 Hz CONH), 7.07–7.35(10H, m, $2C_6H_5$), 7.44 and 8.17(4H, 2d, J 9.0 Hz, $C_6H_4NO_2$) ppm]. The product was dissolved in ethyl acetate (25 mL) and 80 % acetic acid (25 mL) followed by dropwise addition of 4% aqueous potassium permanganate (50 mL) within 1 hour at 0° C. There was added drop-by-drop a solution of 30% aqueous $H_2O_2$ till the colour of the solution was discharged. Organic layer was separated, washed with an aqueous solution of NaHCO₃ and water, dried (Na₂SO₄) and evaporated in vacuum. The residue was purified by column chromatography on silica gel using methylene chloride-ethyl acetate (4:1) as eluant. There was obtained 0.3 g (23.5 %) of sulfonamide m.p. 135°–137° C.: $R_f$ 0.92 (n-BuOH:HOAc:H₂O=4:1:1); IR (KBr)3360m, 3290m, 1770vs, 1655s, 1515m, 1320s, 1135s, 720s cm⁻¹; ¹H NMR (DMSO-d₆) δ:3.56(2H bs, CH₂CO), 4.15–4.20(2H, m, NCH₂), 4.85(1 H, d, J 4.7 Hz, C₂H), 5.57(1H, dd, J 4.7 and 9.5 Hz, C₃H), 7.25 and 7.38(10H, 2 bs, 2C₆H₅), 7.87–7.93(1H, m, SNH), 8.49(1H, d, J 9.5 Hz, CONH) 9.24(1H, bs, N₁H) ppm; Anal.C₁₈H₁₉N₃O₄S calc.: C 57.70, H 5.90, N 11.74, S 8.47% found: C 57.89, H 5.13, N 11.25, S 8.59%.

Example 6

(2R,3R) 1-(1'-Carboxyl-2'methyl-prop-1'-enyl)-2-[(5'-methyl-isoxazol-3'-yl)aminosulfonyl]-3-phenylacetamido-4-oxo-azetidine The p-nitrobenzyl ester of (5R,6R) 6-phenyl-acetamidopenicillanate sulfoxide (3.0 g, 6.2 mmole) was treated with N-chlorosuccinimide (1.0 g, 7.5 mmole) as was described in example 1. and there was added 3-amino-5-methyl-isoxazole (2.4 g, 25 mmole) and reaction mixture stirred within 3 hours at 5° C. The toluene solution was decanted, washed with water, dried and evaporated in vacuum. There was obtained ( 1.43 g) of (2R,3R) 1-(1'-p-nitrobenzyloxycarbonyl-2'-methyl-prop-2'-enyl)-2-[(5'-methyl-isoxazol-3'-yl)aminosulfinyl] -3-phenylacetamido-4-oxo-azetidine [m.p. 157°–160 ° C.; ¹H NMR (CDCl₃) δ:1.93(3H, s, Me), 2.35(3H, s, Me-isoxazole), 3.61(2H, s, CH₂CO), 4.94(1H, bs, NCHCO), 5.07 and 5.19(2H, 2bs, =CH₂), 5.13(1H, d, J 4.8 Hz, C₂H), 5.28(2H, bs, OCH₂), 5.57(1H, bs, CH-isoxazole), 5.77(1H, dd, J 4.8 and 9.0 Hz, C₃H), 7.22(5H, bs, C₆H₅), 7.44(1H, d, J 9.0 Hz, CONH), 7.49 and 8.21 (4H, 2d, J 8.8 Hz, C₆H₄NO₂) ppm], which after stirring with triethylamine in methylene chloride was transformed to (2R,3R) 1-(1' -p-nitro-benzyloxycarbonyl-2'-methyl-prop-1'-enyl)-2-[(5'-methyl-isoxazol-3'-yl) amino sulfinyl]-3-phenylacetamido-4-oxo-azetidine [¹H NMR (CDCl₃) δ:2.18 and 2.22(6H, 2s, CMe₂), 2.34(3H, s, Me-isoxazole), 3.61(2H, s, CH₂CO), 5.11(1H, d, J 4.9 Hz C₂H), 5.25(2H, s, OCH₂), 5.64(1H, dd, J 5.0 and 8.4 Hz, C₃H), 5.63(1H, s, CH-isoxazole), 7.24(5H, s, C₆H₅), 7.26(1H, d, J 8.4 Hz, CONH), 7.47 and 8.18(4H, 2d, J 8.5 Hz, C₆H₄NO₂) ppm]. The obtained sulphinamide was oxidized with hydrogen peroxide as described in example 1. giving (2R,3R) 1-(1'-p-nitrobenzyloxycarbonyl-2'-methyl-prop-1'-enyl)-2-(5' -methyl-isoxazol-3'-yl)aminosulfonyl-3-phenylacetamido-4-oxo-azetidine [$R_f$ 0.57 (CH₂Cl₂: MeOH=8:1); IR (KBr)3680-2500m, 1785s, 1730m, 1665s, 1615m, 1520s, 1350s, 1215m, 1160m cm⁻¹; ¹H NMR (CDCl₃)δ:1.99 and 2.15(6H, 2s, CMe₂), 2.28(3H, s, Me-isoxazole), 3.59(2H, s, CH₂CO), 5.19(2H, s, OCH₂), 5.44(1H, d, J 5.3 Hz, C₂H), 5.81(1H, s, CH-isoxazole), 5.84(1H, dd, J 5.3 and 9.9 Hz, C₃H), 6.84(1H, d, J 9.9 Hz, CONH), 7.28(5H, s, C₆H₅), 7.45 and 8.17(4H, 2d, J 8.9 Hz, C₆H₄NO₂) ppm]. The obtained sulfonamide (0.35 g, 0.6 mmole) was dissolved in methanol (25 mL), there was added 10% Pd/C (50 mg) and reaction mixture treated with hydrogen under pressure (2.4 bar). Reaction mixture was filtered, mother liquor evaporated till dryness. The residue was dissolved in methylene chloride (20 mL) and water (20 mL), the aqueous solution of NaHCO₃ was added till pH 8.5; the aqueous layer separated, washed with methylene chloride, and there was added fresh methylane chloride (15 mL) and hydrochloric acid till pH 2.2. Organic layer was separated, dried (Na₂SO₄) and evaporated under reduced pressure. There was obtained 0.14 g (52.4%) of the product. $R_f$ 0.48 (CH₂Cl₂: MeOH=3:2 ) IR (KBr)3660-2300bm, 2910m, 1790s, 1680bs, 1620s, 1465m, 1270m, 1165m, 930w cm⁻¹; ¹H NMR (CDCl₃) δ:1.93 and 2.07(6H, 2s, CMe₂), 2.35(3H, s, Me-isoxazole), 3.67(2H, s, CH₂CO), 5.68(1H, d, J 5.2 Hz, C₂H), 6.0(1H, dd, J 5.2 and 9.3 Hz, C₃H), 6.12(1H, s, CH-isoxazole), 6.63(1H, d, J 9.3 Hz, CONH), 7.27–7.31 (5H, m, C₆H₅) ppm.

Example 7

(2R,3R ) 1-(1'-m-Methylbenzyloxycarbonyl-2'-methyl-prop-2'-enyl)-2-[(5' -methyl-isoxazol-3'-yl)aminosulfonyl]-3-[(3'-o-chlorophenyl-5'-methyl-isoxazol- 4'-yl)carboxamido]-4-oxo-azetidine The m-methylbenzyl ester of (5R,6R) 6-(3'-o-chlorophenyl-5'-methyl-isoxazol- 4'-yl)carboxamidopenicillanate sulfoxide (2.0 g, 3.6 mmole) was treated with N-chlorosuccinimide as was described in example 1. and 3-amino-5-methyl-isoxazole (1.1 g, 11 mmole) was added and stirred within 3 hours at room temperature. The suspension was filtered and mother liquor washed with water (3×60 mL), dried over Na₂SO₄, filtered and evaporated in vacuum. There was obtained the epimeric mixture (1.92 g) of (2R,3R) 1-(1' -m-methyl-benzyloxycarbonyl-2'-methyl-prop-2'-enyl)-2-[(5'-methyl-isoxazol-3'-yl)aminosulfinyl] -3-[(3'-o-chlorophenyl-5'-methyl-isoxazol-4'-yl)carboxamido]-4-oxo-azetidine [$R_f$ 0.40 and 0.26 in methylene chloride-ethylacetate (4:1)], which was dissolved in methylene chloride and formic acid and oxidized with hydrogen peroxide as described in example 1. The crude product was chromatographed on a silica gel column by means of solvents methylene chloride-ethylacetate. There was isolated 0.62 g (44%) of sulfonamide: $R_f$ 0.55 (CH₂Cl₂:MeOH= 10:1); IR (KBr) 3405w, 1795vs, 1745s, 1680vs, 1620s, 1520s, 1465m, 1385m, 1340m, 1265m, 1160m, 770m cm⁻¹; ¹H NMR (CDCl₃) δ:1.79(3H, s, Me), 2.31 (3H, s, C₆H₅Me), 2.35 and 2.72 (6H,2s, 2Me-isoxazole), 4.85(1H, s, NCHCO), 4.90 and 5.10(2H, 2s, =CH₂), 5.08 and 5.13(2H, ABq, J 12 0 Hz, OCH₂), 5.44(1H, d, J 5.0 Hz, C₂H), 5.95(1H, dd, J 5.0 and 9.6 Hz, C₃H), 6.04(1 H, s, CH-isoxazole), 6.37(1H, d, J 9.6 Hz, CONH), 7.01–7.26 and 7.41–7.55(8H, 2m, 2C₆H₄) ppm.

Example 8

(2R) 1-(1'-Benzyloxycarbonyl-2'-methyl-prop-1'-enyl)-2-benzylaminosulfonyl- 3,3-dibromo-4-oxo-azetidine The benzyl ester of (5R) 6,6-dibromopenicillanate sulfoxide (7.0 g, 15 mmole) was treated with N-chlorosuccinimide as was described in example 1., whereupon the reaction with benzylamine (4 mL, 37.5 mmole) was continued. Reaction mixture was filtered, mother liquor washed with water, dried over Na₂SO₄, filtered and evaporated in vacuum. The crude product was chromatographed on a silica gel column by means of solvents methylene chloride-ethylacetate (6:1). There was isolated 3.08 g (36%) of (2R) 1-(1' -benzyloxycarbonyl-2'-methyl-prop-1'-enyl)-2-benzylaminosulfinyl-3,3-dibromo- 4-oxo-azetidine [¹H NMR (CDCl₃) δ:1.84 and 2.26(6H, 2s, CMe₂), 3.68– 4.40(3H, m, SNHCH₂), 5.07 and 5.24(2H, ABq, J 12 Hz, OCH₂), 5.09(1H, s, C₂H), 7.10–7.30(10H, m, 2C₆H₅) ppm], which was oxidized with m-chloro perbenzoic acid (1.2 g, 6 mmole) in chloroform. Reaction mixture was stirred within 20 minutes at −10° C. and then 1 hour at room temperature. 1M solution of sodium bisulfite (36 mL, 6 mmole) was added, organic layer separated, washed with water, dried over Na$_2$SO$_4$, filtered and evaporated in vacuum. The residue was dissolved in methylene chloride and filtered over a silica gel column giving 2.1 g (59 %) of white crystals: m.p. 120°–122 ° C.: R$_f$ 0.88 (CH$_2$Cl$_2$:EtOAc=4:1); IR (KBr): 3250vs, 1780vs, 1730vs, 1640s, 1440vs, 1370b, 1255s, 1200s, 1165vs, 1055vs, 755vs, 700vs cm$^{-1}$; $^1$H NMR (CDCl$_3$) δ:2.09 and 2.28(6H, 2s, CMe$_2$), 4.09(2H, d, J 5.8 Hz,NCH$_2$C$_6$H$_5$), 4.63(1H, t, J 5.8 Hz, SNH), 5.08 and 5.34(2H, ABq, J 11.7 Hz, OCH$_2$), 5.32(1H, s, C$_2$H), 7.29–7.35(10H, m, 2C$_6$H$_5$) ppm.

Example 9

(2R) 1-(1'-Benzyloxycarbonyl-2'-methyl-prop-1'-enyl)-2-[(5'-methyl-isoxazol-3 '-yl)aminosulfonyl]-3,3-dibromo-4-oxo-azetidine a) The benzyl ester of (5R) 6,6-dibrompenicillanate sulfoxide (7.0 g, 15 mmole) was treated with N-chlorosuccinimide as was described in example 1., thereafter 3-amino-5-methyl-isoxazole (4.47 g, 45 mmole) was added and the reaction mixture stirred within 3 hours at 20 ° C. The solid was separated by filtration, dried, dissolved in methylene chloride (30 mL) and stirred with triethylamine (1.5 mL) within 1 hour at 20 ° C. The reaction mixture was washed with 0.1 N hydrochloric acid (pH 1–2) and water, organic layer dried over Na$_2$SO$_4$, filtered and evaporated in vacuum to give 1.85 g of (2R) 1-(1' -benzyloxy-carbonyl-2'-methyl-prop-1'-enyl)-2-[(5'-methyl-isoxazol-3'-yl)amino-sulfinyl] -3,3-dibromo-4-oxo-azetidine [m.p. 58°–60 ° C.; R$_f$ 0.51 (CH$_2$Cl$_2$:EtOAc-4:1); $^1$H NMR (CDCl$_3$)δ:1.88 and 2.13(6H, 2s, CMe$_2$), 2.31(3H, s, Me-isoxazole), 5.13(2H, s, OCH$_2$), 5.56(1H, s, C$_2$H), 5.67(1H, s, CH-isoxazole), 7.35(5H, s, C$_6$H$_5$) and 8.32(1H, s, SNH) ppm], which was oxidized with m-chloroperbenzoic acid as was described in example 8. The crude product was chromatographed on a silica gel column by means of solvents methylene chloride-ethylacetate (4:1) giving white crystals (52.6 %); m.p. 168°–170° C.: R$_f$ 0.25 (CH$_2$Cl$_2$:EtOAc=4:1); IR (KBr): 3160m, 1780vs, 1765vs, 1625s, 1500s, 1395vs, 1383s, 1220s, 1175vs cm$^{-1}$; $^1$H NMR (CDCl$_3$) δ:2.06 and 2.15(6H, 2s, CMe$_2$), 2.37(3H, s, Me-isoxazole), 5.05(2H, s, OCH$_2$), 5.70(1H, s, C$_2$H), 6.07(1H, s, CH-isoxazole), 7.31(5H, s, C$_6$H$_5$) ppm.

b) Sulfinamide (0.85 g, 1.5 mmol) obtained under above procedure, was dissolved in methylene chloride (5 mL) and formic acid(5 mL), and oxidized with hydrogen peroxide (0.56 mL) within 1 hour at boiling. After cooling, water was added to the reaction mixture, organic layer separated, extracted with 5% aqueous NaHCO$_3$, water, dried (Na$_2$SO$_4$), filtered and evaporated. The obtained product was identical to the product described in the process a).

Example 10

(2R) 1-(1'-Carboxyl-2'-methyl-prop-1'-enyl)-2-benzylaminosulfonyl-3,3 -dibromo-4-oxo-azetidine In the ice cooled suspension of aluminium trichloride (0.4 g, 3 mmole) and methylene chloride (15 mL),in the nitrogen stream, the solution of (2R) 1-(1' -benzyloxycarbonyl-2'-methyl-prop-1'-enyl)-2-benzylaminosulfonyl-3,3 -dibromo-4-okso-azetidine (0.59 g, 1 mmole) and anisole (0.65 g, 6 mmole) in methylene chloride (15 mL) was added and stirred 30 minutes at room temperature. To the reaction solution were added ethylacetate (15 mL) and 0.1 N hydrochloric acid (5 mL). The layers were separated, ethyl acetate layer extracted with 5% sodium hydrogencarbonate (2×20 mL), and again separated. Water layer acidified till pH 1 with 0.1 N hydrochloric acid (5 mL), fresh ethylacetate (20 mL) and NaCl were added and well stirred. The ethylacetate layer was separated, washed with saturated solution of NaCl, dried and evaporated in vacuum.. There was obtained 0.49 g (98 %) m.p. 47°–50 ° C.: R$_f$ 0.66 (EtOAc:MeOH=3:1); IR(film): 3300m, 2960-2930m, 1805vs, 1700s, 1625m, 1425m, 1350s, 1160s cm$^{-1}$; $^1$H NMR (DMSO-d$_6$) ,δ:1.98 and 2.23(6H, 2s, CMe$_2$), 4.09 and 4.20(2H, ABX, J 5.7, 6.0 and 15.2 Hz, CH$_2$C$_6$H$_5$), 5.51(1 H, s, C$_2$H), 7.29–7.39(5H, m, C$_6$H$_5$), 8.49(1H, dd, J 5.7 and 6.0 Hz, NH), 13.5(1H, b, COOH) ppm.

Example 11

(2R) 1-(1'-Carboxyl-2'-methyl-prop-1'-enyl)-2-benzylaminosulfonyl-4 -oxo-azeti-dine (2R) 1-(1'-Benzyloxycarbonyl-2'-methyl-prop-1'-enyl)-4-oxo-azetidin-2-sulfinic acid (3.23 g, 10 mmole) was dissolved in thionylchloride (20 mL) and stirred for 1 hour at 25° C. The excess of thionylchloride was evaporated under reduced pressure till the oily residue, which was dissolved in methylene chloride (50 mL). The solution was cooled at 10° C. and 5% solution of benzylamine in methylene chloride was added drop-by-drop under cooling till pH 7.0 and stirred for another 30 minutes at the same temperature. Benzylamine hydrochloride was separated by filtration and rinsed with methylene chloride. To the mother liquor was added water (50 mL), reaction mixture acidified till pH 1.3 with 10% HCl, organic layer separated, washed with water, dried (Na$_2$SO$_4$) and evaporated till dryness. There was obtained an epimeric mixture (3.85 g, 93 %) of (2R) 1-(1'-benzyloxycarbonyl-2' -methyl-prop-1'-enyl)-2-benzylaminosulfinyl-4-oxo-azeti-dine with R$_f$ 0.64 and 0.72 (CH$_2$Cl$_2$:EtOAc=2:1), which was separated by column chromatography on a silica gel [compound with R$_f$ 0.64: IR (CH$_2$Cl$_2$): 3020vs, 2980s, 1760vs, 1700m, 1415m, 1260vs, 1210s, 1070m, 900s cm$^{-1}$; $^1$H NMR (CDCl$_3$) ,δ:1.95 and 2.24(6H, 2s, CMe$_2$), 3.11(1H, dd, J 5.0 and 15.3 Hz, α C$_3$H), 3.39(1H, dd, J 2.6 and 15.3 Hz, β C$_3$H), 4.0–4.3(3H, m, NHCH$_2$), 4.77(1H, 2d, J 2.6 and 5.0 Hz, C$_2$H), 5.08 and 5.29(2H, ABq, J 12.0 Hz, CH$_2$C$_6$H$_5$), 7.32(10H, s, 2C$_6$H$_5$), ppm;. compound with R$_f$ 0.72: IR (CH$_2$Cl$_2$): 3025vs, 2980s, 1755vs, 1700m, 1420m, 1260 vs, 1210s, 1075m, 900s cm$^{-1}$; $^1$H NMR (CDCl$_3$) δ:2.08 and 2.21(6H, 2s, CMe$_2$), 2.94 and 3.16(2H, 2d, J 3.2 and 4.7 Hz, β C$_3$H and α C$_3$H), 4.19(3H, b, NHCH$_2$), 4.77(1H, dd, J 3.2 and 4.7 Hz, C$_2$H), 5.06 and 5.28(2H, ABq, J 12.3 Hz, CH$_2$C$_6$H$_5$), 7.32(10H, s, 2C$_6$H$_5$) ppm]. Sulfinamide (1.65 g, 4 mmole) reacted with potassium permanganate according procedure in example 5. After a shorter withholding of the permanganate colour the reaction was finished. There was obtained 1.32 g (77%) of (2R) 1-(1' -benzyloxycarbonyl-2'-methyl-prop-1'-enyl)-2-benzylaminosulfonyl-4-oxo-azeti-dine which was purified by silica gel column chromatography by means of solvents CH$_2$Cl$_2$:EtOAc=2:1 [R$_f$ 0.62 (benzen-EtOAc=2:1); m.p. 92°–94° C.; IR (KBr): 3300vs, 1775vs, 1650vs, 1430m, 1350s, 1335s,1290m, 1290vs, 1200m, 1150s, 1070w cm$^{-1}$; $^1$H NMR (CDCl$_3$)δ:2.05 and 2.23(6H, 2s, CMe$_2$), 3.16(2H, d, J 3.8 Hz, α C$_3$H and β C$_3$H), 4.08(2H, d, J 5.9 Hz, NCH$_2$), 4.50(1H t, J 5.9 Hz, NH), 4.89(1H, t, J 3.8 Hz, C$_2$H), 5.09 and 5.18(2H, ABq, J 12.0 Hz, CH$_2$C$_6$H$_5$), 7.25 and 7.34(10H, 2s, 2C$_6$H$_5$) ppm]. The obtained sulfonamide (0.4 g, 1.16 mmol) was hydrogenated and treated according to the procedure in example 6. giving 0.36 g of the acid: R$_f$ 0.88 (n-BuOH:HAc:H$_2$O= 4:1:1); IR (KBr): 3260s, 1760vs, 1700s, 1630m, 1430m, 1330s, 1170s, 1070 cm$^{-1}$. $^1$H NMR (CDCl$_3$) δ:2.09 and 2.26(6H, 2s, CMe$_2$), 3.17(2H, d, J 4.1 Hz, C$_3$H), 4.26(2H, s, NCH$_2$), 4.98(1H, t, J 4.1 Hz, C$_2$H), 7.30(5H, s, C$_6$H$_5$) ppm.

Example 12

(2R) 2-Benzylaminosulfonyl-4-oxo-azetidine a) (2R) 1-(1'-Methyloxycarbonyl-2'-methyl-prop-1'-enyl)-4-oxo-azetidine-2 -sulfinic acid (5.0 g, 20 mmole) was dissolved in thionylchloride (20 ml) and treated as was described in example 11. There was obtained an epimeric mixture (5.4 g, 80.4%) of (2R) 1-(1'-methyloxycarbonyl-2'-methyl-prop-1'-enyl)- 2-benzyl-aminosulfinyl-4-oxo-azetidine with R$_f$ 0.20 and 0.27 (CH$_2$Cl$_2$:EtOAc=2:1), which was separated by silica gel column chromatography [compound with R$_f$ 0.20: IR (CH$_2$Cl$_2$): 3200–3300m, 2930m, 1760vs, 1715s, 1220s, 1080s cm$^{-1}$; $^1$H NMR (CDCl$_3$) δ:1.99 and 2.23(6H, 2s, CMe$_2$), 3.17(1H, dd, J 5.0 and 15.2 Hz, a C$_3$H), 3.46(1H, dd, J 2.6 and 15.2 Hz, b C$_3$H), 3.75(3H, s, OCH$_3$), 4.15–4.30(1H, b, NH), 4.23(2H, s, CH$_2$C$_6$H$_5$), 4.92(1H, 2d, C$_2$H, J 2.6 and 5.0 Hz), 7.31(5H, s, C$_6$H$_5$) ppm; compound with R$_f$ 0.27: IR (CH$_2$Cl$_2$): 3300m, 2950m, 1775vs, 1720s, 1360s, 1220s, 1080s cm$^{-1}$; $^1$H NMR (CDCl$_3$) δ:2.07 and 2.20(6H, 2s, CMe$_2$), 2.97(1H, dd, J 3.1 and 15.5 Hz, β C$_3$H), 3.25(1H, dd, J 5.0 and 15.5 Hz, α C$_3$H), 3.73(3H, s, OCH$_3$), 4.15–4.33(1H, b, NH), 4.26(2H, s, CH$_2$C$_6$H$_5$), 4.83(1H, 2d, J 3.1 and 5.0 Hz, C$_2$H), 7.32(5H, s, C$_6$H$_5$) ppm]. The sulfinamide (3.36 g, 10 mmole) reacted with potassium permanganate according to example 5. To the oily residue (2.5 g) ether (30 ml) was added and the obtained gelatinous mass stirred at room temperature within 8 hours. Crystals were separated and washed with ether; m.p. 111°–130° C.; R$_f$ 0.10 (benzene:EtOAc=3:1); IR (KBr): 3300vs, 1790vs, 1740vs, 1430s, 1330s, 1300s, 1120s, 1070s cm$^{-1}$; $^1$H NMR (DMSO-d$_6$) δ:2.96(3H, dd, J 2.1 and 15.2 Hz, β C$_3$H), 3.29(1H, dd, J 4.7 and 15.2 Hz, α C$_3$H), 4.23(2H, d, J 5.9 Hz, NCH$_2$), 4.71(1H, dd, J 2.1 and 4.7 Hz, C$_2$H), 7.33(5H, s, C$_6$H$_5$), 7.96(1H, t, J 5.9 Hz, SNH), 8.92(1H, s, N$_1$H) ppm.

b) (2R) 1-(1'-Benzyloxycarbonyl-2'-methyl-prop-1'-enyl)-2 -benzyl-amino-sulfonyl-4-oxo-azetidine performed in example 11 reacted with potassium permanganate analogously to example a) whereby the identical product was obtained.

Example 13

(2R) 1-(1'-Carboxyl-2'-methyl-prop-1'-enyl)-2-[(5'-methyl-isoxazol-3' -yl)aminosulfonyl]-4-oxo-azetidine (2R) 1-(1'-Benzyloxycarbonyl-2'-methyl-prop-1'-enyl)-4-oxo-azetidine-2 -sulfinic acid (3.23 g, 10 mmole) was dissolved in thionylchloride (10 mL) and the solution stirred for 1 hour at 25 ° C. The excess of thionylchloride was evaporated under reduced pressure till the oily residue, which was dissolved in methylene chloride (50 mL) and 3-amino-5-methyl-isoxazole (2.94 g, 30 mmole) added and stirred for 3 hours at room temperature. To the reaction mixture water (50 mL) and 10% hydrochloric acid till pH 1.5 were added and the layers were separated. Organic layer washed again with water (50 mL). Water (50 mL) was added to the organic layer and saturated solution of NaHCO$_3$ till pH 8.0. The layers were separated, organic layer washed again with water, dried over Na$_2$SO$_4$ and evaporated till dryness. There was obtained the mixture (3.80 g, 92.6%) of epimers (2R) 1-(1'-benzyloxycarbonyl- 2'-methyl-prop-1'-enyl)-2-[(5'-methyl-isoxazol-3'-yl)aminosulfinyl]-4 -oxo-azetidine, with R$_f$ 0.29 and 0.35 (CH$_2$Cl$_2$:EtOAc=2:1) which were separated by silica gel chromatography [compound with R$_f$ 0.29: IR (CH$_2$Cl$_2$) 1780vs, 1720m, 1620s, 1465s, 1360s, 1290m, 1215s, 1100s, 1080m cm$^{-1}$; $^1$H NMR (CDCl$_3$) δ:1.98 and 2.20(6H, 2s, CMe$_2$), 2.34(3H, s, Me-isoxazole), 3.28(1H, dd, J 4.7 and 15.5 Hz, α C$_3$H), 3.54(1H, dd, J 2.6 and 15.5 Hz, β C$_3$H), 5.06(1H, dd, J 2.6 and 4.7 Hz, C$_2$H), 5.19(2H, s, CH$_2$C$_6$H$_5$), 5.82 (1H, s, CH-isoxazole), 7.33(5H, s, C$_6$H$_5$), 8.40(1H, s, NH) ppm; compound with R$_f$ 0.35: IR (CH$_2$Cl$_2$) 1780vs, 1725m, 1630s, 1470s, 1360m, 1290m, 1220s, 1100s, cm$^{-1}$; $^1$H NMR (CDCl$_3$)δ:2.09 and 2.24(6H, 2s, CMe$_2$), 2.36 (3H, s, Me-isoxazole), 3.04(1H, dd, J 2.9 and 15.5 Hz, β C$_3$H), 3.30(1H, dd, J 5.0 and 15.5 Hz, α C$_3$H), 5.11(1H, dd, J 2.9 and J 5.0 Hz, C$_2$H), 5.21(2H, s, CH$_2$C$_6$H$_5$), 5.80(1H, s, CH-isoxazole), 7.26(5H, s,) ppm.]. A solution of sulfinamide (4.03 g, 10 mmole), m-chloroperbenzoic acid (4.30 g, 25 mmole) and ethyl acetate (50 mL) was stirred at room temperature for 24 hours. There was added drop-by-drop a wather solution of sodium thyosulfate (15 mmole) and stirred for additional 30 minutes. To the reaction mixture was added 5% aqueous sodium bicarbonate till pH 8.5, and the layers separated. The aqueous layer was saturated with sodium chloride and extracted with ethyl acetate (3×30 mL). The combined organic layers washed with brine (30 mL), dried over sodium sulfate and evaporated till dryness. There was obtained 3.5 g (79%) of the crude product as sodium salt. To the solution of crude product in water, 10 % hydrochloric acid was added till pH 2.0 giving (2R) 1-(1' -benzyl-oxycarbonyl- 2'-methyl-prop-1'-enyl)-2-[(5'-methyl-isoxazol-3'-yl)aminosulfonyl] -4-oxo-azetidine.[m.p. 141°–143 ° C.(crystalized from ether); R$_f$ 0.40 (CH$_2$Cl$_2$:EtOAc=2:1); IR (KBr): 3200s, 1790vs, 1720vs, 1620s, 1465s, 1395s, 1300s, 1175s cm$^{-1}$; $^1$H NMR (CDCl$_3$)δ:2.02 and 2.14(6H, 2s, CMe$_2$), 2.37(3H, s, Me-isoxazole), 3.32(2H, d, J 3.5 Hz, α C$_3$H and β C$_3$H), 5.10(2H, s, CH$_2$C$_6$H$_5$), 5.28(1H, t, J 3.5 Hz, C$_2$H), 6.10(1H, s, CH-isoxazole), 7.25 (5H, s, C$_6$H$_5$) ppm; Anal; C$_{19}$H$_{21}$N$_3$O$_6$S found: C, 54.21; H, 5.34; N, 9.96, S, 8.23%; calc. C, 54.41, H, 5.05, N, 10.02, S, 7.64%]. The obtained sulfinamide (419 mg, 1 mmole) hydrogenated and treated as was described in Example 6. There was obtained 227 mg (69%):R$_f$ 0.91 (n-BuOH:HAc:H$_2$O=4:1:1); IR (KBr): 3600-3000b, 3175s, 1795s, 1760s, 1680vs, 1620vs, 1520m, 1470vs, 1400vs, 1310s, 1270m, 1180vs, 1080m, 1045m, cm$^{-1}$; $^1$H NMR (DMSO-d$_6$) δ:1.89 and 2.13(6H, 2s, CMe$_2$), 2.35(3H, s, Me-isoxazole), 3.21(1H, dd, J 1.8 and 15.3 Hz, β C$_3$H), 3.55(1H, dd, J 4.5 and 15.3 Hz, α C$_3$H), 5.34(1H, dd, J 1.8 and 4.5 Hz, C$_2$H), 6.07(1H, s, CH-isoxazole), 11.32(1H, bs, NH), 13.05(1H, b, COOH) ppm.

Example 14

(2R) 1-(1'-Benzyloxycarbonyl-2'-methyl-prop-1'-enyl)-2-[(3',4' -dimethyl-isoxazol-5'-yl)aminosulfonyl]-4-oxo-azetidine (2R) 1-(1'-Benzyloxycarbonyl-2'-methyl-prop-1'-enyl)-4-oxo-azetidine-2 -sulfinic acid (3.23 g, 10 mmole) was dissolved in thionylchloride (10 mL). The solution was stirred 1 hour at 25 ° C. The excess of thionylchloride was evaporated under reduced pressure till the oily residue. The evaporated residue was dissolved in methylene chloride (50 mL), there was added the 5-amino-3,4-dimethyl-isoxazole (3.78 g, 30 mmole) and treated as was noted in example 13. There was obtained the epimeric mixture (3.20 g, 76.7%) of the (2R) 1-(1'-benzyloxycarbonyl-2'-methyl-prop-1'-enyl)-2-[(3',4' -dimethyl-isoxazol-5'-yl) aminosulinyl]-4-oxo-azetidine with R$_f$ 0.31 and 0.38 (CH$_2$Cl$_2$:EtOAc=2:1), which were separated by chromatography on a silica gel column [the compound with R$_f$ 0.31: IR (KBr): 1790vs, 1730m, 1710s, 1650s, 1370(m), 1300m, 1225vs, 1100m cm$^{-1}$; $^1$H NMR (CDCl$_3$) ,δ:1.82, 1.97, 2.16, 2.20(12H, 4s, 4Me), 3.17(1H, d, J 4.1 Hz, a C$_3$H), 3.45(1H, d, J 3.2 Hz, b C$_3$H), 5.04(1H, dd, J 3.2 and 4.1 Hz, C$_2$H), 5.24(2H, s, CH$_2$C$_6$H$_5$), 7.35(5H, s, C$_6$H$_5$), 7.87(1H, s, NH) ppm; the compound with R$_f$ 0.38; IR (KBr): 1785vs, 1730s, 1700s, 1650s, 1370m, 1300m, 1230s, 1100s, cm$^{-1}$; $^1$H NMR (CDCl$_3$) δ:1.81, 2.10, 2.17, 2.24(12H, 4s, 4Me), 3.09(1H, d, J 2.9 Hz, b C$_3$H), 3.34(1H, d, J 5.0 Hz, a C$_3$H), 5.05(1H, dd, J 2.9i5.0 Hz, C$_2$H), 5.20–5.30(3H, m, CH$_2$C$_6$H$_5$ and NH), 7.35(5H, s, C$_6$H$_5$), ppm]. The solution of sulfinamide (4.17, 10 mmole), m-chloroperbenzoic acid (4.3 g, 25 mmole) and ethyl acetate (50 mL) was stirred for 24 hours at room temperature and treated as was noted in example 13. There was obtained 3.2 g (70%) of the product as sodium salt with m.p 160° C.: R$_f$ 0.44 (EtOAc); IR (CH$_2$Cl$_2$): 1790vs, 1730m, 1365s, 1220s, 1170s, 1070m cm$^{-1}$; $^1$H NMR (CDCl$_3$) δ:1.90, 2.03, 2.21, 2.23(12H, 4s, 4Me), 3.29(2H, d, J 4.0 Hz, α C$_3$H and b C$_3$H), 5.17(1H, t, J 4.0 Hz, C$_2$H), 5.24(2H, s, CH$_2$C$_6$H$_5$), 7.35(5H, s, C$_6$H$_5$) ppm.

Example 15

(2R) 1-(1'-Benzyloxycarbonyl-2'-methyl-prop-1'-enyl)-2-[(2'-phenyl-pyrazol-3'-yl)aminosulfonyl]-4-oxo-azetidine (2R) 1-(1'-Benzyloxycarbonyl-2'-methyl-prop-1'-enyl)-4-oxo-azetidine-2-sulfinic acid (10 mmole) was dissolved in thionylchloride (3.23 g, 10 mL), treated as was noted in example 13. and instead of 3-amino-5-methyl-isoxazole the 2-phenyl-3-amino-pyrazole (4.77 g, 30 mmole) was added. There was obtained the mixture (4.04 g, 86%) of epimers (2R) 1-(1'-benzyloxycarbonyl-2'-methyl-prop-1'-enyl)-2-[(2'-phenyl-pyrazol-3'-yl)amino-sulfinyl] -4-oxo-azetidine with R$_f$ 0.44 and 0.50 (CH$_2$Cl$_2$.EtOAc=2:1) which were separated by chromatography on a silica gel column [the compound with R$_f$ 0.44: IR (KBr): 1780vs, 1720s, 1600m, 1500s, 1455m, 1360m, 1290m, 1215vs, 1080m cm$^{-1}$; $^1$H NMR (CDCl$_3$)δ:1.93 and 2.16(6H, 2s, CMe$_2$), 2.96(1H, dd, J 4.9 and 15.3 Hz, α C$_3$H), 3.07(1H, dd, J 2.5 and 15.3 Hz, β C$_3$H), 4.79(1H, dd, J 2.5 and 4.9 Hz, C$_2$H), 5.14(2H, s, CH$_2$C$_6$H$_5$), 6.22 and 7.57(2H, 2d, J 1.9 Hz, =CH—CH=), 7.26–7.45(10H, m, 2C$_6$H$_5$) ppm; the compound with R$_f$ 0.50: IR (KBr): 1780vs, 1720s, 1600m, 1500s, 1455m, 1385m, 1360m, 1290m, 1220s, 1100s, 1070m cm$^{-1}$; $^1$H NMR (CDCl$_3$)δ:2.01 and 2.13(6H, 2s, CMe$_2$), 2.80(1H, dd, J 2.3 and 15.5 Hz, β C$_3$H), 2.92 (1H, dd, J 5.3 and 15.5 Hz, a C$_3$H), 4.80(2H, b, C$_2$H), 5.09 and 5.18(2H, ABq, J 12.4 Hz, CH$_2$C$_6$H$_5$), 6.21 and 7.58(2H, 2d, J 1.6 Hz =CH—CH=), 7.20–7.40 (10H, m 2C$_6$H$_5$) ppm]. The solution of the sulfinamide (4.64 g, 10 mmole), m-chloroperbenzoic acid (4.3 g, 25 mmole) and ethyl acetate (50 mL) was stirred for 24 hours at room temperature and treated as was noted in example 13. There was obtained 3.4 g (67%) of the product as sodium salt: R$_f$ 0.47 (EtOAc); IR (CH$_2$Cl$_2$): 3340w, 1785s, 1725m, 1700m, 1500s, 1390s, 1360s, 1290m, 1215s, 1170s, 1075m cm$^{-1}$; $^1$H NMR (CDCl$_3$) δ:1.96 and 2.16(6H, 2s, CMe$_2$), 2.88(1H, dd, J 5.2 and 15.5 Hz, α C$_3$H), 3.00( 1 H, dd, J 2.3 and 15.5 Hz, β C$_3$H), 4.92(1H, dd, J 2.3 and 5.2, C$_2$H), 5.07 and 5.18(2H, ABq, J 12.1 Hz, CH$_2$C$_6$H$_5$), 6.20 and 7.56(2H, 2d, J 1.7 Hz, =CH—CH=), 7.20–7.40(10H, m, 2C$_6$H$_5$) ppm.

Example 16

(2R,3R) 1-(1'-m-Methylbenzyloxycarbonyl-2'-methyl-prop- 1'-enyl)-2-[(5' -methyl-isoxazol-3'-yl )aminosulfonyl] -3-[(3'-o-chlorophenyl-5'-methyl-isoxazol- 4'-yl)carboxamido]-4-oxo-azetidine The epimeric mixture of sulfinamide (2.24 g), prepared as was noted in example 7, was dissolved in methylene chloride (10 mL) and stirred with triethylamine (0.48 mL) for 2 hours at room temperature. The extraction with 0.1 N hydrochloric acid (5 mL) and water (10 mL) was done. The ogranic extract was dried (Na$_2$SO$_4$), filtered and evaporated in vacuum. There was obtained 2.23 g (99.5%) of a crude product. After a column chromatography on silica gel using CH$_2$Cl$_2$-EtOAc as eluant the (2R,3R) 1-(1' -m-methyl-benzyloxycarbonyl-2'-methyl-prop-1'-enyl)-2-[(5'-methyl-isoxazol-3'-yl)amino-sulfinyl] -3-[(3'-o-chloro-phenyl-5'-methyl-isoxazol-4'-yl)carboxamido]-4 -oxo-azetidine was isolated [R$_f$ 0.21 (CH$_2$Cl$_2$.EtOAc=4:1); m.p. 94°–96° C.; $^1$H NMR (CDCl$_3$) δ:1.95 and 2.22(6H, 2s, CMe$_2$), 2.33 and 2.35(6H, 2s, 2 Me-isoxazole), 2.77(3H, s, Me-C$_6$H$_5$), 4.96(1H, d, J 4.5 Hz, C$_2$H), 5.13 (2H, bs, OCH$_2$), 5.61(1H, dd, J 4.5 and 8.5 Hz, C$_3$H), 5.72(1H, s, CH-isoxazole), 6.69(1H, d, J 8.5 Hz, CONH), 7.04–7.55(8H, m, 2C$_6$H$_4$) ppm] and oxidized with hydrogen peroxyde as was noted in example 1. There was obtained the sulfonamide in 85.8% yield: R$_f$ 0.55 (CH$_2$Cl$_2$:MeOH=10:1); IR(film) 3410w, 3160vw, 3070vw, 1795vs, 1735w, 1685bs, 1620s, 1640m, 1580bs, 1420w, 1300m, 1270m, 1220m, 1170m, 1120m, 1060m, 770m, 740m cm$^{-1}$; $^1$H NMR (CDCl$_3$) δ:1.84 and 2.11 (6H, 2s, CMe$_2$), 2.26 and 2.33(6H, 2s, 2Me-isoxazole), 2.72(3H, s, Me-C$_6$H$_5$), 5.01 (2H, bs, OCH$_2$), 5.36(1H, d, J 5.0 Hz, C$_2$H), 5.71–5.92(2H, m, C$_3$H and CH-isoxazole), 6.41(1H, d, J 10 Hz, CONH), 7.01–7.62(8H, m, 2C$_6$H$_4$) ppm.

Example 17

(2R,3R) 1-(1'-Carboxyl-2'-methyl-prop-1'-enyl)-2-[(5'-methyl-isoxazol-3'-yl)-aminosulfonyl]-3-phthalimido-4-oxo-azetidine a) (2R,3R) 1-(1'-p-Nitrobenzyloxycarbonyl-2'-methyl-prop-2'-enyl)-2-[(5' -methyl-isoxazol-3'-yl)aminosulfinyl]-3-phthalimido-4-oxo-azetidine prepared according to the procedure in example 4., was dissolved in methylene chloride and stirred with triethylamine giving (2R,3R) 1-(1'-p-nitrobenzyloxycarbonyl-2' -methyl-prop-1'-enyl)-2-[(5'-methyl-isoxazol-3'-yl)aminosulfinyl]-3-phthalimido- 4-oxo-azetidine [$^1$H NMR (CDCl$_3$)δ:2.14(6H, bs, CMe$_2$), 2.31(3H, s, Me-isoxazole), 5.08 and 5.23(2H, ABq, J 13.5 Hz, OCH$_2$), 5.58(1H, d, J 5.4 Hz, C$_2$H), 5.71(1H, bs, CH-isoxazole), 6.0(1H, d, J 5.4 Hz, C$_3$H), 7.45 and 8.16(4H, 2d, J 9.0 Hz, C$_6$H$_4$NO$_2$), 7.70–7.94(4H, m, phthalimido) ppm] which after oxidation with hydrogen peroxyde as was noted in example 1. gave (2R,3R) 1-(1'-p-nitro-benzyloxycarbonyl-2'-methyl-prop-1'-enyl)-2-[(5' -methyl-isoxazol-3'-yl)amino-sulfonyl]-3-phthalimido-4-oxo-azetidine [R$_f$ 0.60 (CH$_2$Cl$_2$-:MeOH=9:1); IR(KBr): 1790bs, 1730vs, 1615m, 1520m, 1465m, 1385s, 1350m, 1290w cm$^{-1}$; $^1$H NMR (CDCl$_3$)δ:2.12 and 2.26(6H, 2s, CMe$_2$), 2.32(3H, s, Me-isoxazole), 5.21(2H, bs, OCH$_2$), 5.73(1H, d, J 5.4 Hz, C$_2$H), 5.83(1H, d, J 5.4 Hz, C$_3$H), 6.05(1H, bs, CH-isoxazole), 7.50 and 8.18(4H, 2d, J 9.0 Hz, C$_6$H$_4$NO$_2$), 7.60–7.86(4H, m, phthalimido) ppm.]. The sulfonamide (840 mg, 1.38 mmole) was dissolved in methanol (25 mL), hydrogenated and treated as was described in example 6. From the organic layer upon stirring at room temperature the acid (490 mg, 75%) precipitated with m.p.160°–165° C.: IR(KBr) 3515m, 3200m, 1795s, 1780s, 1735vs, 1685m, 1625m, 1525w, 1475m, 1415m, 1390vs, 1310w, 1180m cm$^{-1}$; $^1$H NMR (DMSO-d$_6$) δ:2.17(6H, s, CMe$_2$), 2.27(3H, s, Me-isoxazole), 3.31(2H, bs, SNH, COOH, HOH), 5.68(1H, d, J 4.9 Hz, C$_2$H), 5.82(1H, d, J 4.9 Hz, C$_3$H), 5.89(1H, s, CH-isoxazole), 7.92(4H, s, phthalimido) ppm.

b) The sulfonamide (0.63 g) obtained in example 4. was dissolved in methylene chloride (10 mL) and stirred with triethylamine (0.1 g) at 10° C. within 5 hours. After a silica gel column chromatography of the evaporated residue there was obtained 0.57 g of sulfonamide which was identical to the product obtained under a) which after hydrogenolyse gave acid.

Example 18

(2R,3R) 1-(1'-p-Nitrobenzyloxycarbonyl-2'-methyl-prop-1'-enyl)-2-[(5' -methyl-isoxazol-3'-yl)aminosulfonyl]-3-amino-4-oxo-azetidine The sulfonamide performed in example 17. was treated with sodium sulfide, followed by dicyclohexylcarbodiimide and finally with methylhydrazine as was described in Croat. Chem.Acta 49 (1977) 779. There was obtained a foamy product which gave positive reaction with ninhydrine: $R_f$ 0.48 ($CH_2Cl_2$:MeOH=9:1) IR (KBr) 1785s, 1735m, 1710m, 1620m, 1525s, 1465w, 1400w, 1150s, 1300w, 1275w, 1220m, 1165m cm$^{-1}$; $^1$H NMR (CDCl$_3$) δ:2.13 and 2.25(6H, 2s, CMe$_2$), 2.39(3H, s, Me-isoxazole), 4.66(1H, d, J 5.2 Hz, C$_2$H), 5.21(1H, d, J 5.2 Hz, C$_3$H), 5.22 and 5.29(2H, ABq, J 12.8 Hz, OCH$_2$), 6.12(1H, s, CH-isoxazole), 7.49 and 8.22(4H, 2d, J 8.5 Hz, C$_6$H$_4$NO$_2$) ppm.

Example 19

(2R,3R) 1-(1'-Carboxyl-2'-methyl-prop-1'-enyl)-2-methylaminosulfonyl-3 -o-methylaminocarbonylphenylcarboxamido-4-oxo-azetidine p-Nitrobenzyl ester of (5R,6R) 6-phthalimidopenicillanate sulfoxide (1.5 g, 3 mmole) was treated with N-chlorosuccinimide (0.4 g, 3 mmole) according to the procedure in example 1., thereafter reaction solution cooled at 5° C. and methylamine (1 mL) added in toluene (4 mL). The reaction mixture was stirred 3 hours at 5° C. and evaporated in vacuum. The residue was suspended in methylene chloride (15 mL), undissolved part was filtered and mother liquor was evaporated in vacuum. There was obtained epimeric mixture (1.53 g) of (2R,3R) 1-(1'-p-nitrobenzyoxycarbonyl-2'-methyl-prop-1'-enyl)-2 -methyl-aminosulfinyl-3-o-methylaminocarbonylphenylcarboxamido-4-oxo-azetidine [IR (film): 3250bm, 3065w, 2950w, 1780s, 1730sh, 1715vs, 1650m, 1605w, 1525s, 1350s, 1295m, 1220m, 1185s, 1060m, 855w, 820w, 740m cm$^{-1}$] which was oxidized with hydrogen peroxide as was noted in example 1. There was obtained 1.23 g of (2R,3R) 1-(1'-p-nitrobenzyoxycarbonyl-2'-methyl-prop-1' -enyl)-2-methyl-aminosulfonyl-3-o-methylaminocarbonylphenylcarboxamido-4 -oxo-azetidine [$R_f$ 0.81(CH$_2$Cl$_2$:MeOH=9:1); $^1$H NMR (CDCl$_3$)δ2.15 and 2.31(6H, 2s, CMe$_2$), 2.86(3H, d, J 4.5 Hz, CONMe), 2.98(3H, d, J 4.9 Hz, SO$_2$NMe), 5.16(1H, d, J 4.9 Hz, C$_2$H), 5.31 and 5.38(2H, ABq, J 13.2 Hz, OCH$_2$), 5.94(1H, dd, J 4.9 and 10.4 Hz, C$_3$H), 6.38(1H, m, SO$_2$NH), 6.97(1H, d, J 10.4Hz, CONH), 7.18(1H, q, J 4.9 Hz, CONH), 7.44–7.52(4H, m, OCC$_6$H$_4$CO), 7.54 and 8.25(4H, 2d, J 8.7 Hz, C$_6$H$_4$NO$_2$) ppm] which by hydrogenolysis, as noted in example 17. gave acid (0.68 g); m.p.142° C. decomp.. IR(KBr):3410m, 3370m, 3170m, 2960m, 1785vs, 1720s, 1680s, 1615s, 1600w, 1560w, 1515m, 1440w, 1415w, 1375w, 1330s, 1315s, 1285s, 1210s, 1185w, 1155w, 1080m, 735m, 700m cm$^{-1}$; $^1$H NMR (DMSO-d$_6$) δ:2.01 and 2.19(6H, 2s, CMe$_2$), 2.64(3H, d, J 4.5 Hz, CONMe), 2.75(3H, d, J 4.7 Hz, SO$_2$NMe), 5.24(1 H, d, J 5.0 Hz, C$_2$H), 5.65(1H, dd, J 5.0 and 8.7 Hz, C$_3$H), 7,17(1H, q, J 4,7 Hz, SO$_2$NH), 7.48–7.56(4H, m, C$_6$H$_4$), 8.38(1H, q, J 4.5 Hz, CONH), 9.07(1H, d, J 8.7 Hz, CONH)ppm.

Example 20

(2R,3R) 1-(1'-Carboxyl-2'-methyl-prop-1'-enyl)-2-benzylaminosulfonyl-3 -phenylacetamido-4-oxo-azetidine p-Nitrobenzyl ester of (5R,6R) 6-phenylacetamidopenicillanate sulfoxide (3.0 g, 6.2 mmole) was treated with N-chlorosuccinimide (0.4 g, 3 mmole) according to the procedure in example 1., thereafter benzylamine (1.3 mL, 12.4 mmole) was added and stirred for 2 hours at 5° C. The toluene solution was decanted, washed with water, dried and evaporated in vacuum. After addition of ethyl acetate the (2R,3R) 1-(1'-p-nitrobenzyloxycarbonyl-2'-methyl-prop-2' -enyl)-2-benzyl-amino-sulfinyl]-3-phenylacetamido-4-oxo-azetidine was precipitated and 1.82 g was filtered off [$^1$H NMR (CDCl$_3$) δ:1.91 (3H, s, Me), 3.48(2H, s, CH$_2$CO), 3.95–4.32(3H, m, SNHCH$_2$), 4.80–5.14(4H, m, NCHCO=CH$_2$, C$_2$H), 5.26(2H, bs, OCH$_2$), 5.87(1H, dd, J 5.0 and 9.8 Hz, C$_3$H), 6,52(1H, d, J 9.8 Hz, CONH), 7.12–7.37(10H, m, 2C$_6$H$_5$), 7.47 and 8.22(4H, 2d, J 8.8 Hz, C$_6$H$_4$NO$_2$) ppm], which was isomerized with triethylamine in methylene chloride yielding (2R,3R) 1-(1' -p-nitrobenzyloxycarbonyl-2'-methyl-prop-1'-enyl)-2-benzylaminosulfinyl-3 -phenylacetamido-4-oxo-azetidine (1.66 g) and oxidized with hydrogen peroxide as was described in example 1. There was obtained (2R,3R) 1-(1' -p-nitrobenzyl-oxycarbonyl-2'-methyl-prop-1'-enyl)-2-benzylaminosulfonyl-3 -phenylacetamido-4-oxo-azetidine (1.57 g) [$R_f$ 0.60 (CH$_2$Cl$_2$:EtOAc=4:1); $^1$H NMR (CDCl$_3$) δ:2.06 and 2.24(6H, 2s, CMe$_2$), 3.59–3.98(5H, m, CH$_2$CO, SNHCH$_2$), 4.67(1H, d, J 5.0 Hz, C$_2$H) 5.21(2H, bs, OCH$_2$), 5.73(1H, dd, J 5.0 and 10.3 Hz, C$_3$H), 6.68(1H, d, J 10.3 Hz, CONH), 7.00–7.36(10H, m, 2C$_6$H$_5$), 7.42 and 8.19(4H, 2d, J 8.8 Hz, C$_6$H$_4$NO$_2$ ) ppm], which was hydrogenated as was described in example 6. There was obtained 0.91 g of the product; $R_f$ 0.38 (CH$_2$Cl$_2$:MeOH=4:1); IR (film): 3500-2300bm, 1785s, 1740-1600bs, 1525m, 1340s, 1270m, 1210m, 1160s, 1070m, 740m, 705s cm$^{-1}$; $^1$H NMR (CDCl$_3$) δ:2.07 and 2.25(6H, 2s, CMe$_2$), 3.56 and 3.64(2H, ABq, J 14.8 Hz, CH$_2$CO), 3.98–4.02(3H, m, SNHCH$_2$), 4.94(1H, d, J 5.2 Hz, C$_2$H), 5.84(1H, dd, J 5.2 and 10.3 Hz, C$_3$H), 6,77(1H, d, J 10.3 Hz, CONH), 7.11–7.37(10H, m, 2C$_6$H$_5$) ppm.

Example 21

(2R,3R) 1-(1'-Carboxyl-2'-methyl-prop-1'-enyl)-2-methylaminosulfonyl-3 -phenylacetamido-4-oxo-azetidine The p-nitrobenzyl ester (5R,6R) of 6-phenylacetamidopenicillanate sulfoxide (3.0 g, 6.2 mmole) was treated with N-chlorosuccinimide (1.0 g, 7.5 mmole) as was noted in example 1. whereupon methylamine (1 mL) was added and reaction mixture was stirred 2 hours at 5° C. The precipitate was filtered off, mother liquor was washed with water, dried and evaporated in vacuum. By column chromatography on silica gel the (2R,3R) 1-(1' -p-nitrobenzyloxycarbonyl-2'-methyl-prop-1'-enyl)-2-methylaminosulfinyl-3 -phenylacetamido-4-oxo-azetidine was isolated(1.63 g) [$^1$ H NMR (CDCl$_3$) δ: 2.12 and 2.26(6H, 2s, CMe$_2$), 2.47(3H, d, J 5.4 Hz, NMe), 3.63(2H, ABq, J 14.9 Hz, CH$_2$CO), 4.68(1H, d, J 5.0 Hz, C$_2$H) 5.28(2H, s, OCH$_2$), 5.80(1H, dd, J 5.0 and 9.9 Hz, C$_3$H), 7.19(1 H, d, J 9.9 Hz, CONH), 7.26–7.38(5H, m, C$_6$H$_5$), 7.50 and 8.24(4H, 2d, J 8.7 Hz, C$_6$H$_4$NO$_2$ ) ppm], which whereupon was oxidized with hydrogen peroxyde as was noted in example 1. The (2R,3R) 1-(1' -p-nitrobenzyloxycarbonyl-2'-methyl-prop-1'-enyl)-2-methylaminosulfonyl-3-phenylacetamido-4-oxo-azetidine was separated (0.98 g) [IR (KBr): 3460-3140bw, 1785s, 1730m, 1700-1675bm, 1610w, 1525s, 1350s, 1220m, 1155m, 1070m, 850w cm$^{-1}$; $^1$H NMR (CDCl$_3$)δ:2.09 and 2.26(6H, 2s, CMe$_2$), 2.46(3H, d, J 5.0 Hz, NMe), 3.17(1 H, q, J 5 Hz, SNH), 3.55 and 3.69(2H, ABq, J 14.5 Hz, CH$_2$CO), 4.97(1H, d, J 5.0 Hz, C$_2$H) 5.27 and 5.33(2H, ABq, J 13.2 Hz, OCH$_2$), 5.80(1H, dd, J 5.2 and 10.3 Hz, C$_3$H), 6.58(1H, d, J 10.3 Hz, CONH), 7.32–7.51(5H, m, C$_6$H$_5$), 7.50 and 8.23(4H, 2d, J 8.7 Hz, C$_6$H$_4$NO$_2$ )-ppm]. The prepared sulfonamide was hydrogenated as noted in example 6. and 0.43 g of acid was separated after hydrogenolysis; IR(KBr): 3660-2440bm, 1785s, 1740-1620bm, 1335m, 1160m, 1075w, 740w, 705w cm$^{-1}$; H NMR (CDCl$_3$) δ:2.07 and 2.25(6H, 2s, CMe$_2$), 2.53(3H, d, J 4.5 Hz, NMe), 3.63(2H, ABq, J 15.1 Hz, CH$_2$CO), 4.16(1H, m, SNH), 5.24(1H, d, J 5.2 Hz, C$_2$H), 5.88(1H, dd, J 5.2 and 10.3 Hz, C$_3$H), 6,84(1H, d, J 10.3 Hz, CONH), 7.26–7.40(5H, m, C$_6$H$_5$) ppm.

Example 22

(2R,3R) 1-(1'-Carboxyl-2'-methyl-prop-1'-enyl)-2-[(5'-methyl-isoxazol-3 '-yl)-aminosulfonyl]-3-phenoxyacetamido-4-oxo-azetidine The p-nitrobenzyl ester of (5R,6R) 6-phenoxyacetamidopenicillanate sulfoxide (5.0 g, 10 mmole) was treated with N-chlorosuccinimide (1.7 g, 13 mmole) as noted in example 1. whereupon 3-amino-5-methyl-isoxazole (4.1 g, 40 mmole) was added and the reaction mixture was stirred 2 hours at 0° C. The toluene solution was decanted, washed with water, dried and evaporated in vacuum. There was obtained the epimeric mixture (5.0 g, 83.6%) of the (2R,3R) 1-(1' -p-nitrobenzyloxycarbonyl-2'-methyl-prop-2'-enyl)-2-[(5'-methyl-isoxazol-3'-yl)-aminosulfinyl] -3-phenoxyacetamido-4-oxo-azetidine [epimer in excess: m.p. 196°–198° C.; IR (KBr): 3310w, 1775s, 1755m, 1665m, 1625m, 1520s, 1350s, 1240m, 1170m, 1100s, 915w, 855w, 755w cm$^{-1}$; $^1$H NMR (CDCl$_3$) δ:2.02 (3H, s, Me), 2.25(3H, s, Me-isoxazole), 4.45 and 4.54 (2H, ABq, J 15.1, OCH$_2$CO), 5.07(1H, bs, NCHCO), 5.07 and 5.19(2H, 2bs, =CH$_2$), 5.39(1H, d, J 5.1 Hz, C$_2$H), 5.35(2H, bs, OCH$_2$), 5.76(1H, bs, CH-isoxazole), 5.85(1H, dd, J 5.0 and 9.0 Hz, C$_3$H), 6.91–7.36(5H, m, C$_6$H$_5$), 7.49(1H, d, CONH), 7.49 and 8.21(4H, 2d, J 8.8 Hz, C$_6$H$_4$NO$_2$) ppm]. The epimeric mixture was oxidized with hydrogen peroxyde as noted in example 1., isomerized with triethylamine in methylene chloride whereupon 3.5 g (68.2%) of the (2R,3R)1-(1' -p-nitrobenzyloxycarbonyl-2'-methyl-prop-1'-enyl)-2-( 5'-methyl-isoxazol-3' -yl)-aminosulfonyl-3-phenoxyacetamido-4-oxo-azetidine was isolated [R$_f$ 0.67 (CH$_2$Cl$_2$: MeOH=9:I); IR (KBr): 3410-2700m, 1795s, 1735m, 1700s, 1620m, 1525m, 1500m, 1465m, 1400m, 1355m, 1300m, 1220s, 1165m, 1065-1110m cm$^{-1}$; $^1$H NMR (CDCl$_3$) δ:2.11 and 2.20(6H, 2s, CMe$_2$), 2.24(3H, s, Me-isoxazole), 4.35 and 4.50(2H, ABq, J 15.1 Hz, OCH$_2$CO). 5.26(2H, s, OCH$_2$), 5.59( 1H, d, J 5.2 Hz, C$_2$H), 6.00(1H, s, CH-isoxazole), 6.03(1H, dd, J 5.2 and 10.5 Hz, C$_3$H), 6.90–7.35(5H, s, OC$_6$H$_5$), 7.52 and 8.22(4H, 2d, J 8.8 Hz, C$_6$H$_4$NO$_2$) ppm]. The sulfonamide (0.56 g, 0.91 mmole) was hydrogenated as noted in example 6. whereupon 0.23 g (52.5%) of the product was isolated: R$_f$ 0.35 (CH$_2$Cl$_2$:MeOH=1.5:1.0) IR (KBr)3600-2400bm, 1795s, 1700bs, 1620m, 1500-1550s, 1235s, 1170s, 1065-1090m, 940m cm$^{-1}$; H NMR (CDCl$_3$) δ:2.05 and 2.19(6H, 2s, CMe$_2$), 2.27(3H, s, Me-isoxazole), 4.50 and 4.59(2H, ABq, J 15.0 Hz, OCH$_2$CO), 5.78(1H, d, J 4.8 Hz, C$_2$H), 6.09(1H, dd, J 4.8 and 10.5 Hz, C$_3$H), 6.23(1H, s, CH-izoksazol), 6.91–7.40(5H, m, OC$_6$H$_5$), 7.78(1H, d, J 10.5 Hz, CONH) ppm.

We claim:
1. Oxo-azetidine-2-sulfonic acid amides and their salts of formula I

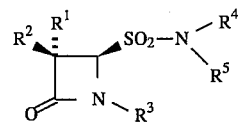

selected from the group consisting of compounds wherein R$^1$ stands for hydrogen, R$^2$ stands for hydrogen, R$^3$ stands for Me$_2$C=C—COOCH$_2$C$_6$H$_5$, R$^4$ stands for hydrogen and R$^5$ stands for C$_6$H$_5$CH$_2$;

wherein R$^1$ stands for hydrogen, R$^2$ stands for hydrogen, R$^3$ stands for Me$_2$C=C— COOCH$_2$C$_6$H$_5$, R$^4$ stands for sodium and R$^5$ stands for C$_6$H$_5$CH$_2$;

wherein R$^1$ stands for hydrogen, R$^2$ stands for hydrogen, R$^3$ stands for hydrogen, R$^4$ stands for hydrogen and R$^5$ stands for C$_6$H$_5$CH$_2$;

wherein R$^1$ stands for bromine, R$^2$ stands for hydrogen, R$^3$ stands for Me$_2$C=C— COOCH$_2$C$_6$H$_5$, R$^4$ stands for hydrogen and R$^5$ stands for C$_6$H$_5$CH$_2$;

wherein R$^1$ stands for hydrogen, R$^2$ stands for bromine, R$^3$ stands for Me$_2$C=C— COOCH$_2$C$_6$H$_5$, R$^4$ stands for hydrogen and R$^5$ stands for C$_6$H$_5$CH$_2$;

wherein R$^1$ stands for bromine, R$^2$ stands for bromine, R$^3$ stands for Me$_2$C=C— COOCH$_2$C$_6$H$_5$, R$^4$ stands for hydrogen and R$^5$ stands for C$_6$H$_5$CH$_2$;

wherein R$^1$ stands for bromine, R$^2$ stands for bromine, R$^3$ stands for Me$_2$C=C— COOCH$_2$C$_6$H$_5$, R$^4$ stands for sodium and R$^5$ stands for C$_6$H$_5$CH$_2$;

wherein R$^1$ stands for hydrogen, R$^2$ stands for hydrogen, R$^3$ stands for Me$_2$C=C— COOCH$_2$C$_6$H$_5$, R$^4$ stands for hydrogen and R$^5$ stands for 5-methyl-isoxazol-3-yl;

wherein R$^1$ stands for bromine, R$^2$ stands for bromine, R$^3$ stands for Me$_2$C=C— COOCH$_2$C$_6$H$_5$, R$^4$ stands for hydrogen and R$^5$ stands for 5-methyl-isoxazol-3-yl;

wherein R$^1$ stands for hydrogen, R$^2$ stands for C$_6$H$_5$OCH$_2$CONH, R$^3$ stands for Me$_2$C=C—COOMe, R$^4$ stands for hydrogen and R$^5$ stands for C$_6$H$_5$CH$_2$;

wherein R$^1$ stands for hydrogen, R$^2$ stands for C$_6$H$_5$OCH$_2$CONH, R$^3$ stands for Me$_2$C=C—COOMe, R$^4$ stands for hydrogen and R$^5$ stands for 5-methyl-isoxazol-3-yl;

wherein R$^1$ stands for hydrogen, R$^2$ stands for phthalimido, R$^3$ stands for Me$_2$C=C— COOCH$_2$C$_6$H$_4$NO$_2$-p, R$^4$ stands for hydrogen and R$^5$ stands for 5-methyl-isoxazol-3-yl;

wherein R$^1$ stands for hydrogen, R$^2$ stands for C$_6$H$_5$CH$_2$CONH, R$^3$ stands for hydrogen, R$^4$ stands for hydrogen and R$^5$ stands for C$_6$H$_5$CH$_2$;

wherein R$^1$ stands for hydrogen, R$^2$ stands for C$_6$H$_5$CH$_2$CONH, R$^3$ stands for Me$_2$C=C—COOCH$_2$C$_6$H$_4$NO$_2$-p, R$^4$ stands for hydrogen and R$^5$ stands for 5-methyl-isoxazol-3-yl;

wherein R$^1$ stands for hydrogen, R$^2$ stands for C$_6$H$_5$CH$_2$CONH, R$^3$ stands for Me$_2$C=C—COOH, R$^4$ stands for hydrogen and R$^5$ stands for 5-methyl-isoxazol-3-yl;

wherein R$^1$ stands for hydrogen, R$^2$ stands for hydrogen, R$^3$ stands for Me$_2$C=C—COOH, R$^4$ stands for hydrogen and $R^5$ stands for $C_6H_5CH_2$;

wherein $R^1$ stands for hydrogen, $R^2$ stands for 3-o-chlorophenyl-5-methyl-isoxazol-4-yl, $R^3$ stands for $H_2C=C(Me)-CH-COOCH_2C_6H_4Me-m$, $R^4$ stands for hydrogen and $R^5$ stands for 5-methyl-isoxazol-3-yl;

wherein $R^1$ stands for hydrogen, $R^2$ stands for o-MeNHCOC$_6$H$_4$CONH, $R^3$ stands for $Me_2C=C-COOCH_2C_6H_4NO_2$-p, $R^4$ stands for hydrogen and $R^5$ stands for methyl;

wherein $R^1$ stands for hydrogen, $R^2$ stands for o-MeNHCOC$_6$H$_4$CONH, $R^3$ stands for $H_2C=C(Me)-CH-COOCH_2C_6H_4NO_2$-p, $R^4$ stands for hydrogen and $R^5$ stands for methyl;

wherein $R^1$ stands for hydrogen, $R^2$ stands for o-MeNHCOC$_6$H$_4$CONH, $R^3$ stands for $Me_2C=C-COOH$, $R^4$ stands for hydrogen and $R^5$ stands for methyl;

wherein $R^1$ stands for hydrogen, $R^2$ stands for $C_6H_5CH_2CONH$, $R^3$ stands for $Me_2C=C-COOH$, $R^4$ stands for hydrogen and $R^5$ stands for $C_6H_5CH_2$;

wherein $R^1$ stands for hydrogen, $R^2$ stands for $C_6H_5CH_2CONH$, $R^3$ stands for $Me_2C=C-COOCH_2C_6H_4NO_2$-p, $R^4$ stands for hydrogen and $R^5$ stands for $C_6H_5CH_2$;

wherein $R^1$ stands for hydrogen, $R^2$ stands for $C_6H_5CH_2CONH$, $R^3$ stands for $Me_2C=C-COOCH_2C_6H_4NO_2$-p, $R^4$ stands for hydrogen and $R^5$ stands for methyl;

wherein $R^1$ stands for hydrogen, $R^2$ stands for $C_6H_5CH_2CONH$, $R^3$ stands for $Me_2C=C-COOH$, $R^4$ stands for hydrogen and $R^5$ stands for methyl;

wherein $R^1$ stands for hydrogen, $R^2$ stands for hydrogen, $R^3$ stands for $Me_2C=C-COOH$, $R^4$ stands for hydrogen and $R^5$ stands for 5-methyl-isoxazol-3-yl;

wherein $R^1$ stands for bromine, $R^2$ stands for bromine, $R^3$ stands for $Me_2C=C-COOH$, $R^4$ stands for hydrogen and $R^5$ stands for $C_6H_5CH_2$; and wherein $R^1$ stands for hydrogen, $R^2$ stands for $C_6H_5OCH_2CONH$, $R^3$ stands for $Me_2C=C-COOH$, $R^4$ stands for hydrogen and $R^5$ stands for 5-methyl-isoxazol-3-yl.

2. A substance as claimed in claim 1, wherein $R^1$ stands for hydrogen, $R^2$ stands for hydrogen, $R^3$ stands for $Me_2C=C-COOCH_2C_6H_5$, $R^4$ stands for hydrogen and $R^5$ stands for $C_6H_5CH_2$.

3. A substance as claimed in claim 1, wherein $R^1$ stands for hydrogen, $R^2$ stands for hydrogen, $R^3$ stands for $Me_2C=C-COOCH_2C_6H_5$, $R^4$ stands for sodium and $R^5$ stands for $C_6H_5CH_2$.

4. A substance as claimed in claim 1, wherein $R^1$ stands for hydrogen, $R^2$ stands for hydrogen, $R^3$ stands for hydrogen, $R^4$ stands for hydrogen, and $R^5$ stands for $C_6H_5CH_2$.

5. A substance as claimed in claim 1, wherein $R^1$ stands for bromine, $R^2$ stands for hydrogen, $R^3$ stands for $Me_2C=C-COOCH_2C_6H_5$, $R^4$ stands for hydrogen and $R^5$ stands for $C_6H_5CH_2$.

6. A substance as claimed in claim 1, wherein $R^1$ stands for hydrogen, $R^2$ stands for bromine, $R^3$ stands for $Me_2C=C-COOCH_2C_6H_5$, $R^4$ stands for hydrogen and $R^5$ stands for $C_6H_5CH_2$.

7. A substance as claimed in claim 1, wherein $R^1$ stands for bromine, $R^2$ stands for bromine, $R^3$ stands for $Me_2C=C-COOCH_2C_6H_5$, $R^4$ stands for hydrogen and $R^5$ stands for $C_6H_5CH_2$.

8. A substance as claimed in claim 1, wherein $R^1$ stands for bromine, $R^2$ stands for bromine, $R^3$ stands for $Me_2C=C-COOCH_2C_6H_5$, $R^4$ stands for sodium and $R^5$ stands for $C_6H_5CH_2$.

9. A substance as claimed in claim 1, wherein $R^1$ stands for hydrogen, $R^2$ stands for hydrogen, $R^3$ stands for $Me_2C=C-COOCH_2C_6H_5$, $R^4$ stands for hydrogen and $R^5$ stands for 5-methyl-isoxazol-3-yl.

10. A substance as claimed in claim 1 wherein $R^1$ stands for hydrogen, $R^2$ stands for $C_6H_5CH_2CONH$, $R^3$ stands for $Me_2C=C-COOCH_2C_6H_4NO_2$-p, $R^4$ stands for hydrogen and $R^5$ stands for $C_6H_5CH_2$.

11. A substance as claimed in claim 1, wherein $R^1$ stands for bromine, $R^2$ stands for bromine, $R^3$ stands for $Me_2C=C-COOCH_2C_6H_5$, $R^4$ stands for hydrogen and $R^5$ stands for 5-methyl-isoxazol-3-yl.

12. A substance as claimed in claim 1, wherein $R^1$ stands for bromine, $R^2$ stands for bromine, $R^3$ stands for $Me_2C=C-COOH$, $R^4$ stands for hydrogen and $R^5$ stands for $C_6H_5CH_2$.

13. A substance as claimed in claim 1 wherein $R^1$ stands for hydrogen, $R^2$ stands for hydrogen, $R^3$ stands for $Me_2C=C-COOH$, $R^4$ stands for hydrogen and $R^5$ stands for 5-methyl-isoxazol-3-yl.

14. A substance as claimed in claim 1 wherein $R^1$ stands for hydrogen, $R^2$ stands for $C_6H_5CH_2CONH$, $R^3$ stands for $Me_2C=C-COOH$, $R^4$ stands for hydrogen and $R^5$ stands for methyl.

15. A substance as claimed in claim 1 wherein $R^1$ stands for hydrogen, $R^2$ stands for $C_6H_5CH_2CONH$, $R^3$ stands for $Me_2C=C-COOCH_2C_6H_4NO_2$-p, $R^4$ stands for hydrogen and $R^5$ stands for methyl.

16. A substance as claimed in claim 1 wherein $R^1$ stands for hydrogen, $R^2$ stands for $C_6H_5OCH_2CONH$, $R^3$ stands for $Me_2C=C-COOMe$, $R^4$ stands for hydrogen and $R^5$ stands for $C_6H_5CH_2$.

17. A substance as claimed in claim 1 wherein $R^1$ stands for hydrogen, $R^2$ stands for $C_6H_5CH_2CONH$, $R^3$ stands for $Me_2C=C-COOH$, $R^4$ stands for hydrogen and $R^5$ stands for $C_6H_5CH_2$.

18. A substance as claimed in claim 1 wherein $R^1$ stands for hydrogen, $R^2$ stands for $C_6H_5OCH_2CONH$, $R^3$ stands for $Me_2C=C-COOMe$, $R^4$ stands for hydrogen and $R^5$ stands for 5-methyl-isoxazol-3-yl.

19. A substance as claimed in claim 1 wherein $R^1$ stands for hydrogen, $R^2$ stands for o-MeNHCOC$_6$H$_4$CONH, $R^3$ stands for $Me_2C=C-COOH$, $R^4$ stands for hydrogen and $R^5$ stands for methyl.

20. A substance as claimed in claim 1 wherein $R^1$ stands for hydrogen, $R^2$ stands for phthalimido, $R^3$ stands for $Me_2C=C-COOCH_2C_6H_4NO_2$-p, $R^4$ stands for hydrogen and $R^5$ stands for 5-methyl-isoxazol-3-yl.

21. A substance as claimed in claim 1, wherein $R^1$ stands for hydrogen, $R^2$ stands for $C_6H_5CH_2CONH$, $R^3$ stands for hydrogen, $R^4$ stands for hydrogen and $R^5$ stands for $C_6H_5CH_2$.

22. A substance as claimed in claim 1, wherein $R^1$ stands for hydrogen, $R^2$ stands for $C_6H_5CH_2CONH$, $R^3$ stands for $Me_2C=C-COOCH_2C_6H_4NO_2$-p, $R^4$ stands for hydrogen and $R^5$ stands for 5-methyl-isoxazol-3-yl.

23. A substance as claimed in claim 1, wherein $R^1$ stands for hydrogen, $R^2$ stands for $C_6H_5CH_2CONH$, $R^3$ stands for $Me_2C=C-COOH$, $R^4$ stands for hydrogen and $R^5$ stands for 5-methyl-isoxazol-3-yl.

24. A substance as claimed in claim 1, wherein $R^1$ stands for hydrogen, $R^2$ stands for hydrogen, $R^3$ stands for $Me_2C=C-COOH$, $R^4$ stands for hydrogen and $R^5$ stands for $C_6H_5CH_2$.

25. A substance as claimed in claim 1, wherein $R^1$ stands for hydrogen, $R^2$ stands for 3-o-chlorophenyl-5-methyl-isoxazol-4-yl, $R^3$ stands for $H_2C=C(Me)-CH-COOCH_2C_6H_4Me$-m, $R^4$ stands for hydrogen and $R^5$ stands for 5-methyl-isoxazol-3-yl.

26. A substance as claimed in claim 1, wherein $R^1$ stands for hydrogen, $R^2$ stands for o-MeNHCOC$_6$H$_4$CONH, $R^3$ stands for $Me_2C=C-COOCH_2C_6H_4NO_2$-p, $R^4$ stands for hydrogen and $R^5$ stands for methyl.

27. A substance as claimed in claim 1, wherein $R^1$ stands for hydrogen, $R^2$ stands for o-MeNHCOC$_6$H$_4$CONH, $R^3$ stands for $H_2C=C(Me)-CH-COOCH_2C_6H_4NO_2$-p, $R^4$ stands for hydrogen and $R^5$ stands for methyl.

28. A substance as claimed in claim 1, wherein $R^1$ stands for hydrogen, $R^2$ stands for $C_6H_5OCH_2CONH$, $R^3$ stands for $Me_2C=C-COOH$, $R^4$ stands for hydrogen and $R^5$ stands for 5-methyl-isoxazol-3-yl.

29. A pharmaceutical composition possessing antimicrobial activity, comprising an antimicrobial effective amount of a compound as claimed in claim 1 and in addition a suitable pharmaceutical excipient.

* * * * *